United States Patent [19]

Gaddy

[11] 3,958,568

[45] May 25, 1976

[54] STANDING TABLE FOR PARAPLEGICS

[76] Inventor: Jerry C. Gaddy, 55 W. Washington Ave., Unit C37, Yakima, Wash. 98902

[22] Filed: May 9, 1975

[21] Appl. No.: 576,203

[52] U.S. Cl. .............................. 128/80 R; 128/80 G

[51] Int. Cl.$^2$ .............................. A61F 3/00

[58] Field of Search .................. 128/80 R, 80 G, 83, 128/87, 68, 84 R, 82; 248/127, 132, 146–151; 272/57 R

[56] References Cited

UNITED STATES PATENTS

| | | | |
|---|---|---|---|
| 2,210,269 | 8/1940 | Taylor | 128/80 R |
| 3,249,368 | 5/1966 | Ginzburg | 128/84 R |
| 3,293,667 | 12/1966 | Ohrberg | 128/68 X |
| 3,750,659 | 8/1973 | Loomans | 128/80 R |

*Primary Examiner*—John D. Yasko
*Attorney, Agent, or Firm*—Clarence A. O'Brien; Harvey B. Jacobson

[57] ABSTRACT

A generally rectangular table is provided including an upper top and four depending supportive corner legs. A first pair of the legs comprise front legs and foot stall defining structure is anchored relative to the lower ends of the front or forward legs and may rest upon a support surface upon which the lower ends of the front legs rest. A generally knee height transverse brace extends between and is supported from the forward legs intermediate their upper and lower ends. Further, an elongated at least somewhat flexible waist retraint member is anchored at one end portion relative to an upper end of one of the front legs and the other end portion of the restraint member and the table include coacting structure operative to releasably anchor the other end portion of the restraint member relative to the upper end portion of the other front leg with the restraint member generally horizontally disposed and in a slightly forwardly bowed condition. However, the restraint member is of sufficient length to extend downwardly from the upper end of the first front leg to a position at least closely adjacent the lower ends of the front legs and to then extend upwardly to the upper end portion of the other front leg when the restraint member is in a slack condition. Still further, the upper end portions of the front legs include forwardly projecting handgrips.

11 Claims, 4 Drawing Figures

STANDING TABLE FOR PARAPLEGICS

BACKGROUND OF THE INVENTION

Many paraplegics are disabled to the extent that they are incapable of standing adjacent a table in an unassisted manner for work at the table. Consequently, many paraplegics of this type have in the past been required to work while seated adjacent a table in a wheelchair. While working at a table in a seated position may in some instances be comfortable to a paraplegic, there are physical conditions of some paraplegics which give rise to extreme discomfort if they are forced to work at a table while seated for extended periods of time. Accordingly, a need exists for providing a means whereby a paraplegic unable to stand in an unassisted manner may be supported adjacent a table for work thereon.

Various types of structures have been heretofore designed to enable a paraplegic unable to stand without assistance to remain in a standing position without the assistance of another person. Examples of such structures as well as structures specifically designed for other purposes in maintaining persons in upright positions are disclosed in U.S. Pat. Nos. 1,530,519, 3,557,782 and 3,750,659.

SUMMARY OF THE INVENTION

The standing table of the instant invention has been specifically designed to enable a paraplegic who is unable to stand in an unassisted manner to readily attain a standing position adjacent the table from a seated position in an adjacent wheelchair. Further, the table is constructed in a manner whereby a paraplegic, after once attaining a standing position adjacent the table may readily releasably brace himself in his standing position.

Further, the table is constructed in a manner whereby a paraplegic standing and braced adjacent the table may, without another person's assistance, release himself from a braced position relative to the table and thereafter lower himself in a convenient manner into his wheelchair.

The main object of this invention is to provide a table specifically designed to enable a paraplegic seated in a wheelchair adjacent the table to attain, without assistance from another person, a standing position adjacent the table and to brace himself in standing position relative to the table in a manner to fully free his arms for work at the table independent of any requirement of his arms to maintain his standing position.

Another object of this invention, in accordance with the immediately preceding object, is to provide a table constructed in a manner whereby a paraplegic standing in braced position adjacent the table may release himself from a braced position relative to the table and lower himself, without assistance from another person, into his adjacent wheelchair.

Another important object of this invention is to provide a table in accordance with the preceding objects and constructed in a manner whereby it may be readily partially disassembled for storage in a compact state.

A still further object of this invention is to provide a table including structural features thereof which may be readily varied in dimension so as to construct a table adaptable for use by persons of different height.

A final object of this invention to be specifically enumerated herein is to provide a table in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
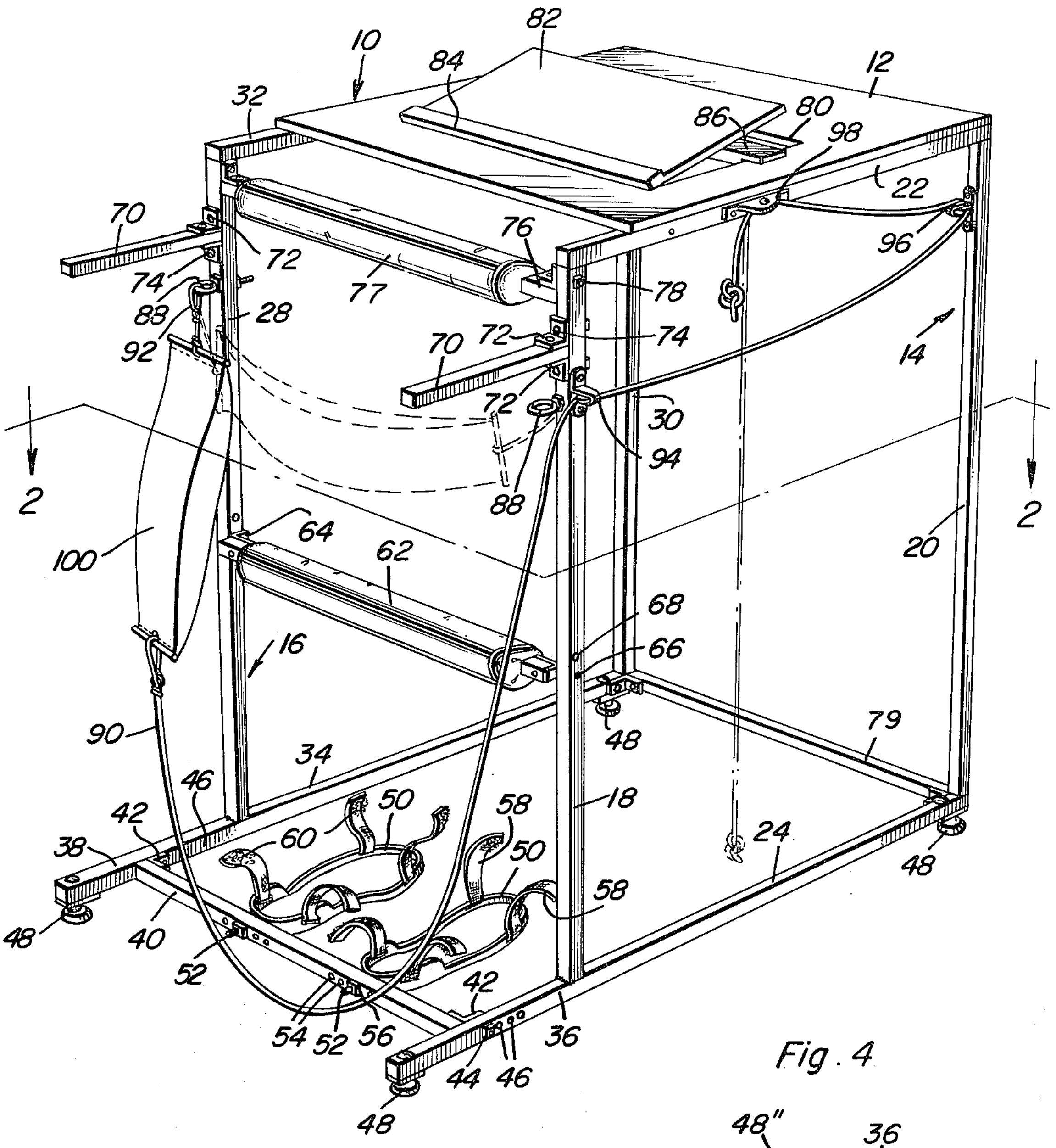
FIG. 1 is a perspective view of the table of the instant invention with the waist restraint portion thereof in a slack position.
Figure 4:
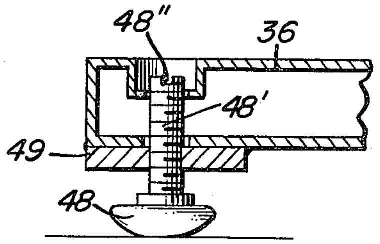
FIG. 4 is a fragmentary vertical sectional view illustrating one of the adjustable feet of the table.
Figure 2:
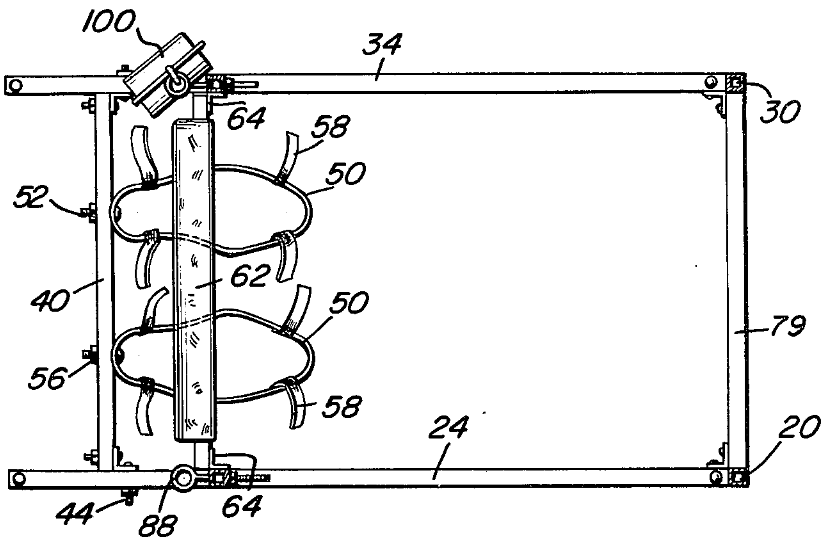
FIG. 2 is a horizontal sectional view on somewhat reduced scale taken substantially upon a plane indicated by the section line 2—2 of FIG. 1.

Referring now more specifically to the drawings, the numeral 10 generally designates the table of the instant invention including a generally horizontal tapletop 12 extending between and secured to a pair of upstanding opposite side frames referred to in general by the reference numerals 14 and 16.

The frame 14 includes upstanding front and rear legs 18 and 20 interconnected at their upper ends by means of a front-to-rear extending upper horizontal brace 22 having its opposite ends secured to the upper ends of the legs 18 and 20 and a lower brace 24 also extending in a front-to-rear direction and having the lower ends of the legs 18 and 20 secured to the front and rear end portions thereof. The frame 16 includes a pair of upstanding legs 28 and 30 corresponding to the legs 18 and 20 and upper and lower braces 32 and 34 corresponding to the braces 22 and 24.

The tabletop 12 is secured over the front-to-rear extending braces 22 and 32 in any convenient manner whereby the tabletop 12 may be released from engagement with the braces 22 and 32 and it will be noted that the forward ends of the lower braces 24 and 34 includes forward extensions 36 and 38 projecting forwardly of the lower ends of the legs 18 and 28 and interconnected intermediate their opposite ends by means of a transverse brace 40. The opposite ends of the transverse brace 40 have L-shaped brackets 42 secured thereto and the brackets 42 are removably fastened, as by means of threaded fasteners 44, through selected longitudinally spaced bores 46 formed through the extensions 36 and 38.

The front and rear ends of the lower braces 24 and 34 include foot members 48 carried by the lower ends of threaded shanks 48' threaded through nuts 49 secured to the under side of the braces 24 and 34 and the upper ends of the shanks 48' include screw driver blade receiving kerfs 48'' whereby the table 10 may be adjusted for stable support from an uneven supporting surface upon which the foot members 48 rest and foot or shoe stalls 50 have rearwardly projecting threaded studs 52 supported from the heel portions of the stalls 50 secured through selected longitudinally spaced bores 54 formed through the brace member 40 by means of threaded nuts 56. The shoe or foot stalls 50 include front and rear pairs of opposite side strap members 58 having corresponding ends secured to the foot stalls 50 and free end portions equipped with "Velcro" type fastening means 60 whereby the strap members 58 may be utilized to secure the shoes of a paraplegic within the foot stalls 50.

A horizontally disposed and transversely extending padded knee brace 62 extends between and has its opposite ends supported from the mid-portions of the front legs 18 and 28. The opposite ends of the knee brace 62 include L-shaped mounting brackets 64 secured, as by means of fasteners 66, through selected transverse bores 68 formed through the legs 18 and 28. It will of course be appreciated that by fastening the knee brace 62 to the legs 18 and 28 by means of the L-shaped brackets 64 and fasteners 66 the knee brace may be positioned in any one of four relatively angularly displaced positions. With the knee brace 62 mounted as illustrated in FIG. 1, the knee brace 62 is in a forwardly displaced position supported by means of the fasteners 66 secured through the lowermost pair of bores 68. However, the knee brace 62 may be angularly displaced through successive 90° rotated positions in order to rearwardly and upwardly displace the knee brace 62, thereafter rearwardly and downwardly displace the knee brace 62 and to finally downwardly and forwardly displace the knee brace 62. In addition, the overall height of the knee brace 62 may be increased vertically by securing the fasteners 66 through the upper set of bores 68.

The upper ends of the legs 18 and 28 include forwardly projecting generally horizontal handgrips 70 with each handgrip 70 being supported in selected vertically shifted position from the corresponding leg by means of a pair of upper and lower angle brackets 72. Further, each of the legs 18 and 28 is provided with a plurality of sets of vertically spaced bores through which fasteners 74 may be secured in order to adjustably vertically position the handgrips 70.

Figure 3:
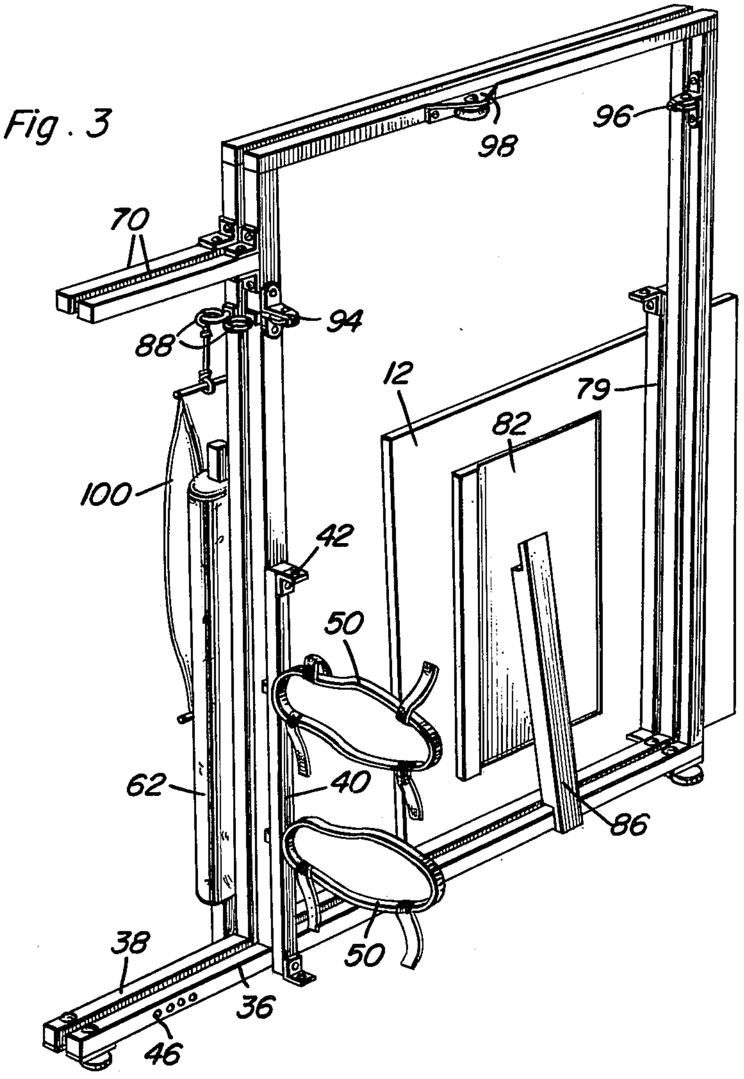
FIG. 3 is a perspective view of the table with various components thereof in a partially disassembled condition for compact storage and transport of the table.

An upper horizontal brace 76, padded as at 77, is also secured between the upper ends of the legs 18 and 28 by means of removable fasteners 78 and a rear lower transverse brace 79 is removably secured between the rear ends of the lower front-to-rear extending braces 24 and 34. Accordingly, when the tabletop 12 is removed, the braces or transverse members 40, 76 and 79 as well as the transverse knee brace 62 may be removed and the components of the table 10 may be arranged in a partially disassembled position such as that illustrated in FIG. 3 of the drawings for compact storage and transport if desired. Of course, the spacing between the foot stalls 50 may be adjusted as desired and the foot stalls 50 may be removed from engagement with the transverse member 40 for storage or shipment, if desired.

The tabletop 12 includes an opening 80 formed therein in which a support panel 82 is recessed. The forward marginal edge portion 84 of the panel 82 is hingedly supported from the portion of the tabletop 12 defining the forward marginal portion of the opening 80 and accordingly, the panel 82 may have its rear marginal edge portion swung upwardly to or past the elevated position thereof illustrated in FIG. 1 of the drawings. Further, a notched abutment bar 86 is provided for bridging the opposite sides of the opening 80 and propping the panel 82 in adjusted position, the bar 86 being slidable longitudinally of those portions of the tabletop 12 defining the opposite side marginal portions of the opening 80.

A pair of anchor eyes 88 have their threaded shank portions secured through upper end portions of the legs 18 and 28 closely spaced below the handgrip 70. One end of an elongated flexible waist restraint member 90 is removably anchored, as by means of a spring clip 92, to the anchor eye 88 supported from the leg 28 and the other end of the restraint member 90 is slidably guidingly received through first and second guide structures 94 and 96 carried by the upper end portions of the legs 18 and 20 as well as a third guide structure and friction locking device 98 carried by an intermediate portion of the brace 22. Further, the end portion of the waist restraint member 90 adjacent the eye member supported from the leg 28 includes a section 100 thereof which is padded and is adapted to be engaged behind the lower waist portion of a person standing at the front of the table 10.

In operation, once the table 10 has been assembled and the vertically adjustable foot members 48 thereof have been adjusted as required, a person seated in a wheelchair may propel his wheelchair up to the front of the table 10. Then, the person may remove his feet from the foot supports on the wheelchair and place his shoes within the shoe stalls 50 and secure the straps 58 over his shoes. In this manner, the person's shoes will be securely anchored to the foot stalls 50. Thereafter, the person seated in the wheelchair and having his feet anchored within the foot stalls 50 may grasp the handgrips 70 and pull himself into an erect standing position at the front of the table 10.

In removing his feet from the foot supports on the wheelchair and placing his shoes within the foot stalls 50, the person using the table 10 passes his shoes over the lower looped portion of the waist restraint member 90 when the latter is positioned as illustrated in FIG. 1 of the drawings. Then, after the person has raised himself into a standing position at the front of the table with the forward portion of his knees abutted against the knee brace 62, the free end portion of the waist restraint member 90 adjacent the guide structure 98 is pulled forwardly in order to tighten the waist restraint member 90 in back of his lower waist portion with the section 100 of the waist restraint member 90 in a slightly forwardly bowed position and immediately behind his lower waist portion. In this manner, the waist restraint member, the knee brace 62 and the foot stalls 50 are operative to retain the person using the table 10 in an upright position. After the proper tension has been placed on the waist restraint member 90, by the device 98, the person using the table 10 is securely braced relative thereto in a standing position and his arms may be used as desired without requiring support from his arms to maintain a standing position at the table 10.

When it is desired, the person using the table 10 may brace himself relative to the table 10 with one hand and with his other hand he may release the free end of the waist restraint member 90 in order that the latter may return to the slack position thereof illustrated in FIG. 1 of the drawings. Then, through the utilization of both hands on the handgrips 70 the person using the table may gently lower himself into his wheelchair. Thereafter, the straps 58 may be released from engagement with his shoes and he may place his feet upon the foot supports of his wheelchair before movement away from the table 10.

The table top 12 may have various other types of table tops (not shown) substituted therefor and such other tops may include various different structural features to assist the user of the table to perform functions.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A standing table for paraplegics, said table including an upper top having a first marginal edge portion and a pair of upright supportive legs spaced along said marginal edge portion and from whose upper ends said top is supported, foot stall defining means anchored relative to said legs and adapted to rest upon a support surface upon which the lower ends rest, a generally knee height transverse brace extending between and supported from said legs below said top, and an elongated at least somewhat flexible waist restraint member anchored at one end portion relative to the upper end portion of one of said legs above said transverse brace, the other end portion of said restraint member and said table including coacting means operative to releasably anchor the other end portion of said restraint member relative to the upper end portion of the other of said legs above said transverse brace, said restraint member being of a length to hang downwardly from said one end portion to a level at least closely adjacent the lower ends of said legs and then extend upwardly to the upper end portion of said other leg, said coacting means including means operative to anchor portions of said other end portion spaced indiscriminately therealong relative to said other leg.

2. The combination of claim 1 wherein said restraint member includes a padded elongated member comprising a length of said restraint member adjacent the point of anchoring of said restraint member relative to said one leg and of a length to extend at least a major portion of the spacing between the upper ends of said legs.

3. The combination of claim 1 wherein each of said legs includes an outwardly projecting handgrip adjacent the upper end thereof below said top.

4. The combination of claim 1 wherein said top includes a work supporting member recessed therein, said work supporting member including a first marginal edge portion adjacent said first marginal edge of said top, means pivotally supporting said first marginal edge portion of said work supporting member from said top for adjustable upward swinging of the remote marginal edge portion thereof to selected levels above said tabletop.

5. The combination of claim 1 wherein said tabletop includes front, rear and opposite side marginal edge portions, said first marginal edge portion comprising said front marginal edge portion, a second pair of upstanding legs supported at their upper end portions from rear marginal edge portions at points spaced therealong.

6. The combination of claim 5 wherein corresponding front and rear legs comprise upright members of opposite side frames each including front-to-rear extending upper and lower brace members extending between and secured to the upper and lower ends of the corresponding front and rear legs, said top and said transverse brace being removably secured between the upper ends of said frames and said front legs, respectively.

7. The combination of claim 5 wherein said coacting means operative to releasably anchor said other end portion of said restraint member relative to said other of said legs includes first guide means carried by said other leg and second guide means supported from said table forward of said other leg, said other end portion of said restraint member being slidingly and guidingly engaged with said first and second guide means, and a forward portion of said table including means relative to which the free end portion of said other end portion of said restraint member may be anchored.

8. The combination of claim 7 wherein said restraint member includes a padded elongated member comprising a length of said restraint member adjacent the point of anchoring of said restraint member relative to said one leg and of a length to extend at least a major portion of the spacing between the upper ends of said legs.

9. The combination of claim 8 wherein each of said legs includes an outwardly projecting handgrip adjacent the upper end thereof below said top.

10. The combination of claim 8 wherein said top includes a work supporting member recessed therein, said work supporting member including a first marginal edge portion adjacent said first marginal edge of said top, means pivotally supporting said first marginal edge portion of said work supporting member from said top for adjustable upward swinging of the remote marginal edge portion thereof to selected levels above said tabletop.

11. The combination of claim 10 wherein corresponding front and rear legs comprise upright members of opposite side frames each including front-to-rear extending upper and lower brace members extending between and secured to the upper and lower ends of the corresponding front and rear legs, said top and said transverse brace being removably secured between the upper ends of said frames and said front legs, respectively.

* * * * *